US00PP15411P2

(12) United States Plant Patent
Olesen et al.

(10) Patent No.: US PP15,411 P2
(45) Date of Patent: Dec. 7, 2004

(54) CLIMBING ROSE PLANT NAMED 'POULYC009'

(50) Latin Name: *Rosa hybrid*
Varietal Denomination: POULyc009

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,759

(22) Filed: Mar. 29, 2004

(51) Int. Cl.[7] ..... A01H 5/00
(52) U.S. Cl. ..... Plt./115
(58) Field of Search ..... Plt./115

*Primary Examiner*—Anne Marie Grunberg
*Assistant Examiner*—Annette H Para

(57) ABSTRACT

A new garden rose plant of the climber class which has abundant, medium red flowers and attractive foliage. This new and distinct variety has shown to be uniform and stable in the resulting generations from asexual propagation.

2 Drawing Sheets

Botanical classification: Rosa hybrid.
Variety denomination: 'POULyc009'.

SUMMARY OF THE INVENTION

The present invention constitutes a new and distinct variety of garden rose plant which originated from a controlled crossing between the female seed parent, an unnamed seedling, and the male pollen parent 'Poulket'. The two parents were crossed during the summer of 1992 and the resulting seeds were planted in a controlled environment in Fredensborg, Denmark. The new variety is named 'Poulyc009'.

The new variety may be distinguished from its female seed parent by the following combination of characteristics:

1. While the seed parent has a medium flower size, between 10 and 15 cm; 'Poulyc009' has a small flower size, between 5 and 8 cm.
2. While the seed parent has a red-orange flower color; 'Poulyc009' has flowers which are medium red in color.

The new variety may be distinguished from its male pollen parent, 'Poulket' by the following combination of characteristics:

1. 'Poulket' has a different growth habit than 'Poulyc009'.
2. 'Poulket' has dark red flowers while 'Poulyc009' has medium red flowers.

The objective of the hybridization of this rose variety was to create a new and distinct variety for garden use with unique qualities, such as:

1. Uniform and abundant medium red flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventors, and distinguish 'Poulyc009' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'Poulyc009' was selected in the spring of 1993 by the inventors as a single plant from the progeny of the aforementioned hybridization.

Asexual reproduction of 'Poulyc009' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'Poulyc009' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulyc009'. Specifically illustrated in the drawing FIG. 1:

FIG. 1.1; Open flower viewed from above, cluster of open flowers, showing branching, and the attachment of leaves, buds, and peduncles;

FIG. 1.2; Flower bud closed, flower bud as sepals unfold, and partially open;

FIG. 1.3; Flower petals, detached;

Specifically illustrated in FIG. 2:

FIG. 2.1; Sepals, receptacle, and peduncle;

FIG. 2.2; Leaves;

FIG. 2.3; Bare stems.

DETAILED DESCRIPTION OF THE VARIETY

The following is a description of 'Poulyc009', as observed in its growth in a field nursery in Jackson County, Oreg. Observed plants are 3 years of age, and were grown on *Rosa multiflora* understock. Color references are made using The Royal Horticultural Society (London, England) Colour Chart, 1995, except where common terms of color are used.

For a comparison, several physical characteristics of the rose variety 'Poulnorm', a rose variety from the same inventors described and illustrated in U.S. Plant Pat. No. 12,552 and issued on Apr. 16, 2002, are compared to 'Poulyc009' in Chart 1.

CHART 1

| | 'Poulyc009' | 'Poulnorm' |
|---|---|---|
| Flower Bud Size upon opening. | 28 mm. | 20 mm–30 mm. |
| Bud form. | Pointed ovoid. | Pointed ovoid. |
| Sepals color. | Yellow-Green Group 144B with marginal intonations of Greyed-Red Group 181C. | Green Group 143C, with intonations on inner side of sepals of Greyed-Red Group 180A. |
| General tonality | Red-Purple 58B to 58C | Red Group 53A |

FLOWER AND FLOWER BUD

Blooming habit: Continuous.

Flower bud:

*Size.*—Upon opening, 28 mm in length from base of receptacle to end of bud. Diameter is 12 mm.

*Bud form.*—Pointed ovoid.

*Bud color.*—As sepals unfold, petals are Red Group 53B. At ¼ opening petals are Red Group 53C.

*Sepals.*—Upper Surface: Color: Yellow-Green Group 145B. Marginal intonations of Greyed-Red Group 181C. Surface: Strongly pubescent. Lower Surface: Color: Yellow-Green Group 144A. Anthocyanic pigments the color of Greyed-Purple Group 185A observed. Texture: Smooth with few stipitate glands. Sepal Shape: Sepal apex is cirrhose. Base is flat at union with peduncle. Sepal Margin: Margins have medium foliaceous appendages on three of the five sepals. Size: 22 mm long by 10 mm wide.

*Receptacle.*—Texture: Smooth and lightly pubescent. Shape: Urn-shaped. Size: 7 mm (h)×7 mm (w). Color: Yellow-Green Group 144A. Anthocyanic pigments the color of Greyed-Orange Group 177A observed.

*Peduncle.*—Surface: Stipitate glands in medium quantity. Length: 35 mm to 40 mm average length. Color: Yellow-Green Group 144B. Anthocyanic pigments the color of Greyed-Red Group 178A observed. Strength: Strong.

*Borne.*—In clusters of 9 flower buds per stem. Reduced apical dominance in flower habit causes flower buds develop evenly from the base of the plant to the upper branches.

Flower bloom:

*Fragrance.*—Moderate rose.

*Duration.*—The blooms have a duration on the plant of approximately 10 to 14 days. Petals fall cleanly away from plant after flowers have completely matured.

*Size.*—Flower diameter is 70 mm when open. Flower depth is 35 mm.

*Form.*—General: Open cup. Side View: Upon opening, upper part: Flat. Upon opening, lower part: Concave. Open flower, upper part: Flat. Open flower, lower part: Concave.

*Petalage.*—Average range is 25 petals under normal conditions with 5 petaloids.

Color:

*Upon opening, petals.*—Outermost petals: Outer side: Red-Purple Group 61C to 63A. Inner side: Red-Purple Group 58B. Innermost petals: Outer side: Red-Purple Group 61C to Red-Purple Group 63A. Inner side: Red-Purple Group 58B.

*Upon opening, basal petal spots.*—No distinctive coloration at the petal base observed. After opening, petals: Outermost petals: Outer side: Red-Purple Group 61C to 63A. Inner side: Red-Purple Group 58B. Innermost petals: Outer side: Red-Purple Group 61C to Red-Purple Group 63A. Inner side: Red-Purple Group 58B.

*After opening, basal petal spots.*—No distinctive coloration at the petal base observed.

General tonality: On open flower Red-Purple 58B to 58C. After the $10^{th}$ day general tonality is Red-Purple Group 58B.

Petals:

*Petal reflex.*—Somewhat reflexed.

*Margin.*—Entire. Medium undulations of margin observed.

*Shape.*—Apex is round. Base is acute to rounded.

*Size.*—50 mm (l)×55 mm (w).

*Texture.*—Smooth.

*Thickness.*—Thick.

*Arrangement.*—Formal.

Petaloids:

*Quantity.*—4 to 7.

*Shape.*—Acute base. Rounded apex.

*Color.*—Upper surface: Red-Purple Group 58B. Lower surface: Red-Purple Group 61C to 63A.

*Size.*—29 mm long×29 mm wide.

Reproductive organs:

*Pollen.*—None observed.

*Anthers.*—Size: 2 mm in length. Color: Greyed-Yellow Group 162A. Quantity: 106 actual count.

*Filaments.*—Color: Yellow Group 4B with intonations of Red Group 52D. Length: 8 mm.

*Pistils.*—Length: 8 mm long. Quantity: 58 (actual count).

*Stigmas.*—Level in location relative to the length of the filaments and the height of the anthers. Color: Greyed-Yellow Group 160D.

*Styles.*—Color: Yellow-Green Group 145C. At top of styles, streaks of Red Group 53C observed.

*Hips.*—None observed in the field nursery in Jackson County, Oreg.

PLANT

Plant growth: Moderate, upright to bushy. When grown as a budded field grown plant on *Rosa multiflora* understock, the average height of the plant is 150 cm to 200 cm. When grown as a nursery plant on its own roots the average plant height 150 cm to 200 cm.

Stems:

*Color.*—Young wood: Yellow-Green Group 146C with anthocyanic intonations of Greyed-Orange Group 177A. Older wood: Yellow-Green Group 146C.

*Surface texture.*—Young wood: Smooth. Older wood: Smooth.

Thorns:

*Incidence.*—2 thorns per 10 cm of stem.

*Size.*—Average length: 8 mm.

*Color.*—Greyed-Orange Group 177B.

*Shape.*—Concave.

Plant foliage: Normal number of leaflets on normal leaves in middle of the stem: 5 leaflets.

*Compound leaf size.*—150 mm (l)×115 mm (w).

*Color.*—Mature Foliage: Upper surface is Yellow-Green Group 147A. Lower surface is Yellow-Green Group 146B. Juvenile foliage: Upper surface is Yellow-Green Group 147A. Lower surface is Yellow-Green Group 146B.

Plant leaves and leaflets:

*Stipules.*—Size: 25 mm in length. Quantity: 2 per compound leaf. Shape: Linear, slightly broad based with outward extending apecies. Margins: Finely serrated with few stipitate glands. Color: Green Group 143B with anthocyanic coloration Greyed-Red Group 180B.

*Petiole.*—Length: 35 mm to 45 mm. Color: Yellow-Green Group 144B with anthocyanic intonations the color of Greyed-Red 180A.

*Rachis.*—Length: 45 mm to 55 mm. Color: Yellow-Green Group 144B with anthocyanic intonations the color of Greyed-Red 180A. Underneath: Small thorns observed.

*Leaflet.*—Edge: Serrated. Size: 60 mm (l)×45 mm (w). Shape: Base is rounded. Apex is cuspidate. Texture: Leathery. Thickness: Thick. Arrangement: Odd pinnate. Venation: Reticulate. Glossiness: Very glossy.

Disease resistance: Above average resistance to mildew, rust, black spot, and Botrytis under normal growing conditions in Jackson County, Oreg.

Cold hardiness: The variety 'Poulyc009' has been found to be cold tolerant to USDA Cold Hardiness Zone 6.

It is claimed:

1. A new and distinct variety of rose plant of the climber rose class named 'Poulyc009', illustrated and described herein as a distinct and novel rose variety due to its abundant medium red flowers, exceptional flowering habit, disease resistance, and extended period of bloom.

* * * * *

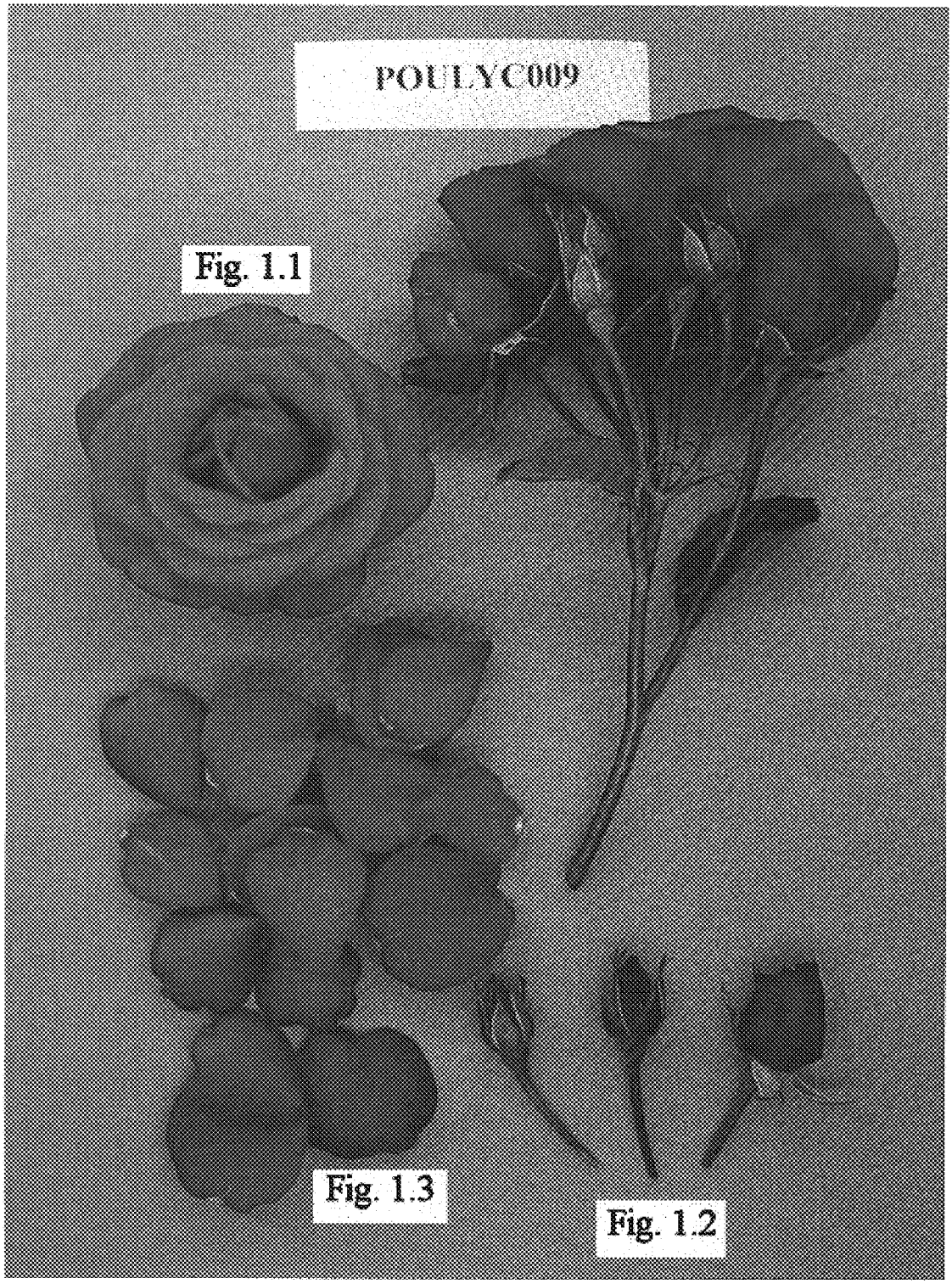
POULYC009
Fig. 1.1
Fig. 1.3
Fig. 1.2

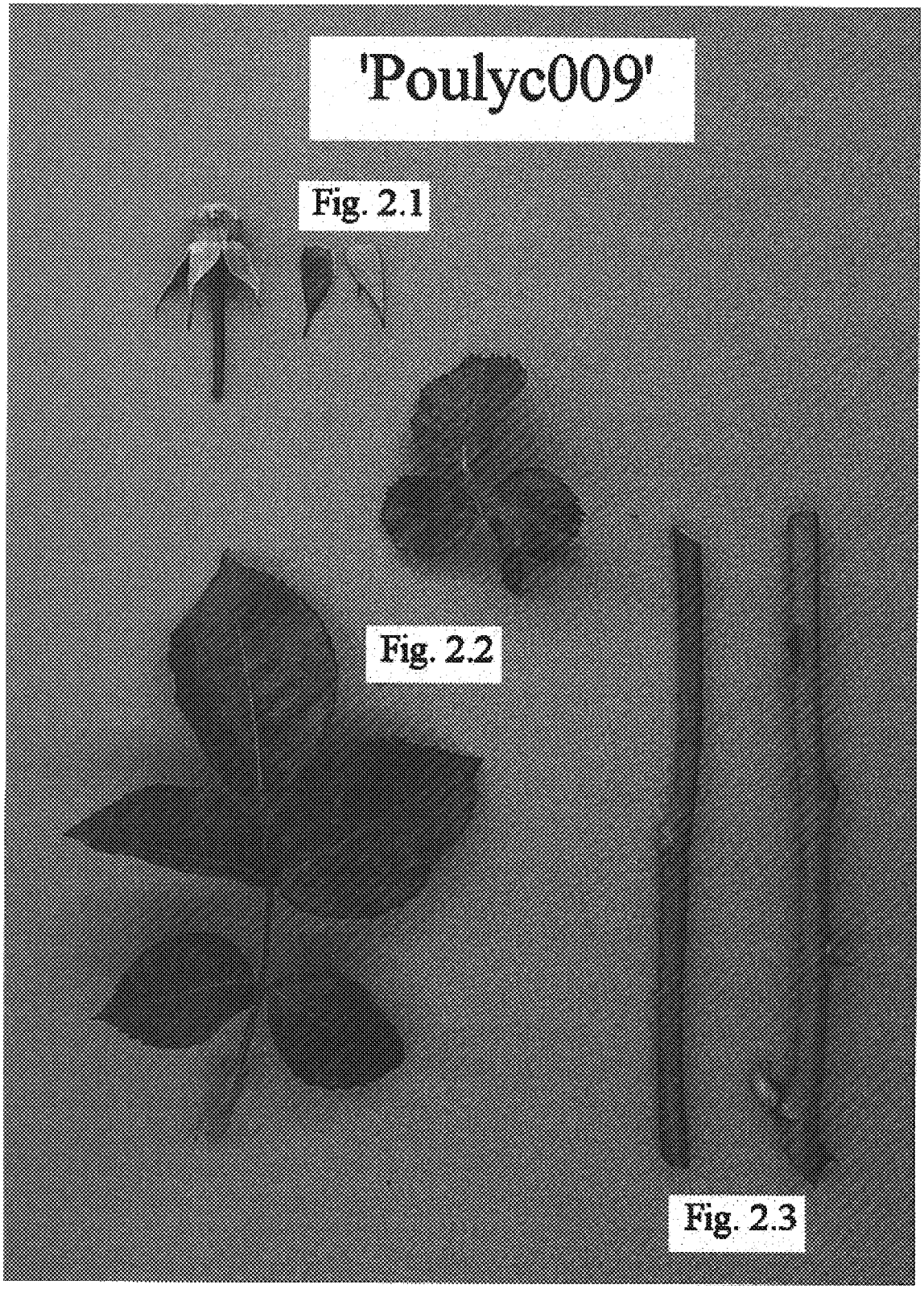
'Poulyc009'
Fig. 2.1
Fig. 2.2
Fig. 2.3